United States Patent [19]
Hauger et al.

[11] Patent Number: 5,775,337
[45] Date of Patent: Jul. 7, 1998

[54] IMMOBILIZATION DEVICE

[75] Inventors: Todd Hauger; Loren G. Kamstra. both of Orange City. Iowa

[73] Assignee: Biotek. Orange City. Iowa

[21] Appl. No.: 821,331

[22] Filed: Mar. 21, 1997

[51] Int. Cl.$^6$ .................................................. A61B 19/00
[52] U.S. Cl. ........................................ 128/869; 5/637
[58] Field of Search ............................. 128/845, 846, 128/869, 870, DIG. 23; 602/17; 5/621, 622, 636, 637; 606/130

[56] References Cited

U.S. PATENT DOCUMENTS

| | | | |
|---|---|---|---|
| 4,550,713 | 11/1985 | Hyman | 128/849 |
| 4,655,206 | 4/1987 | Moody | 128/870 |
| 5,370,117 | 12/1994 | McLaurin | 128/845 |
| 5,531,229 | 7/1996 | Dean | 128/845 |

*Primary Examiner*—Michael A. Brown
*Attorney, Agent, or Firm*—Zarley.McKee.Thomte.Voorhees. & Sease

[57] ABSTRACT

The head and neck immobilization device of the present invention includes a U-shaped frame and a snap-fit insert having a sheet of thermoplastic material bonded thereto. The assembled frame and insert are adapted for indexed mounting on a baseplate of a radiation therapy or diagnostic imaging table. Numerous disposable inserts with formed masks for different patients can be used with the single frame.

20 Claims, 5 Drawing Sheets

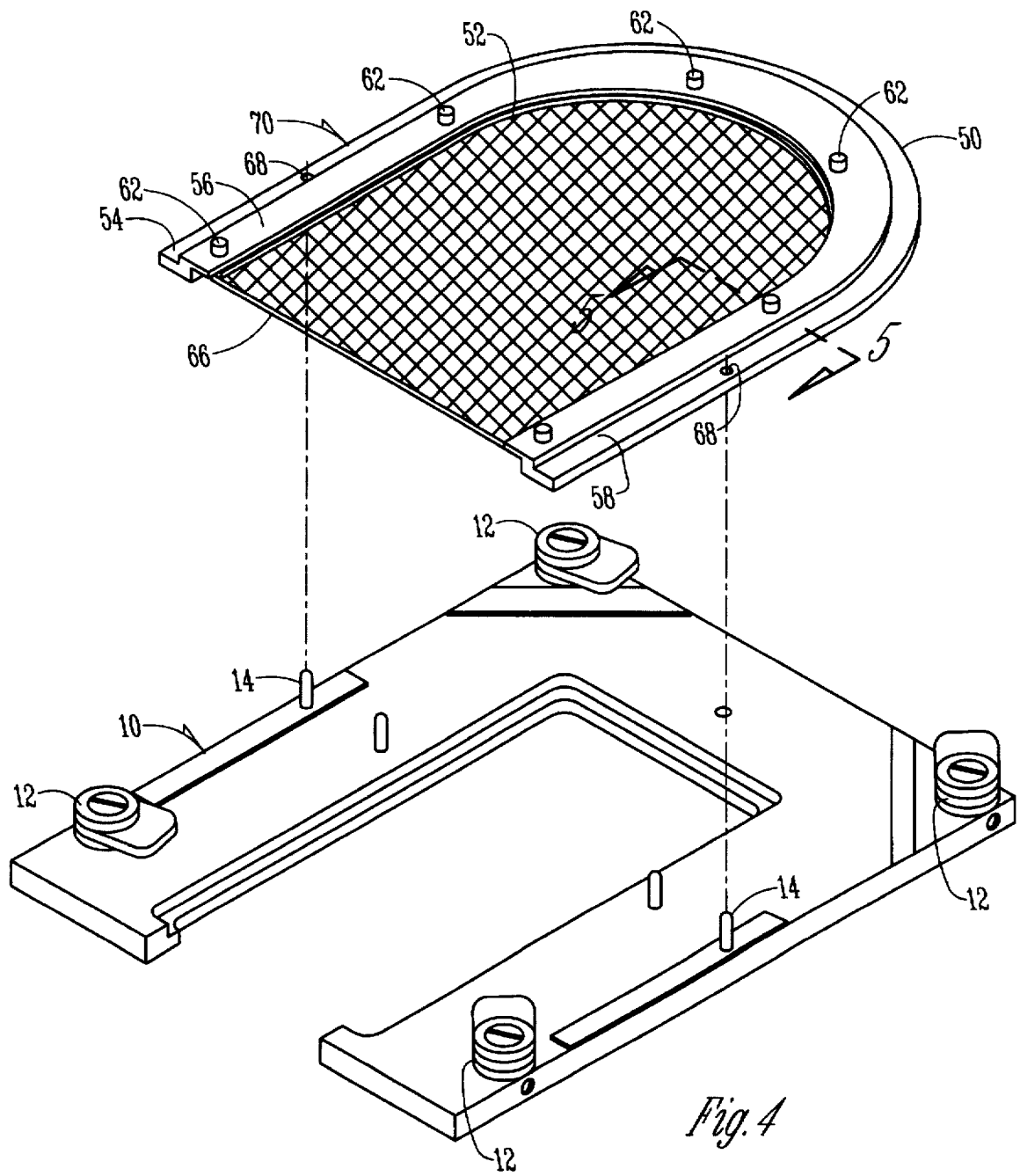

IMMOBILIZATION DEVICE

BACKGROUND OF THE INVENTION

During certain medical procedures, such as radiation therapy treatment, diagnostic imaging, and some surgeries, it is important to immobilize a part or parts of the patient's body. Accurate positioning of the body part is also important in repeat treatments so that the precise same location of the body is exposed to the radiation each time. Therefore, different types of devices have been made to immobilize body parts and to index the body to the treatment table to assure proper and repeatable alignment for radiation therapy.

The present invention is specifically directed toward a device for immobilizing the head and neck of a patient. Typically, a low-temperature thermoplastic deformable sheet material is used to form a mask over the patient's head. The sheet, which is a mesh material b $^1/_{16}$–$^3/_{16}$ inches thick, is heated in warm water so as to soften the material. The material can then be molded around and over the patient's head. When the material cools, a rigid mask is formed.

When the material is softened, it is limp and difficult to control. Therefore, frames are used to hold and control the softened material while it is stretched and deformed into the mask. The frames also allow the hardened mask to be secured to a baseplate on the therapy table.

Prior art head and neck immobilization devices or systems are generally of two different types: a reusable frame and a disposable frame. The reusable frame comprises two frame members between which the thermoplastic sheet material is sandwiched and held through a series of screws in the frame members. Reusable frame systems have several problems. First, since each patient has a separate and unique mask to fit their particular head and facial features, a separate costly frame assembly is required for each patient. Secondly, approximately one inch of thermoplastic material, which is expensive, must be provided on each side to assure adequate retention of the material. Thirdly, it is time consuming to assemble the frame members with the plurality of screws to hold the sheet material.

In the disposable frame system, a single U-shaped frame is used with the thermoplastic sheet being adhered to the plastic frame using pressure sensitive double-sided tape or silicon adhesive. The disposable frame has several problems, such as the cost of the frame which is discarded after use, and the excessive amount of surface area of the thermoplastic sheet which is required for proper adhesion to the frame. Also, the adhesives used with the disposable frame have a possibility of slippage or breakage of the bond between the thermoplastic sheet and the frame, thereby resulting in a poorly made mold or mask.

Therefore, a primary objective of the present invention is the provision of an improved head and neck immobilization device for use in radiation therapy, diagnostic imaging, and surgical procedures.

Another objective of the present invention is the provision of a head and neck immobilization device which minimizes the quantity of thermoplastic sheet material.

A further objective of the present invention is the provision of a head and neck immobilization device having a single frame which can be used with numerous masks for different patients.

Still another objective of the present invention is the provision of a head and neck immobilization device wherein the thermoplastic sheet material is bonded to an insert which is snap-fit into the frame for quick and easy changing of masks.

Yet another objective of the present invention is the provision of a method of immobilizing the head of a patient using the improved immobilization device.

Another objective of the present invention is the provision of a head and neck immobilization device which is safe and durable in use and economical to manufacture.

These and other objectives will become apparent from the following description of the invention.

SUMMARY OF THE INVENTION

The head and neck immobilization device of the present invention includes a U-shaped frame which is sized to extend around the sides and top of a patient's head. The U-shaped insert is adapted to matingly mount within the frame. A sheet of thermoplastic material is attached or bonded to the insert, and is deformable to form a mask over the patient's head. The frame and the insert are snap-fit together for mounting on a conventional baseplate on a radiation therapy treatment table or the like.

Numerous inserts having different molded masks for different patients can be assembled with a single U-shaped frame, thereby minimizing the costs to the institutions. Also, the bonding of the sheet material to the insert requires approximately ¼ inch overlap, thereby minimizing the amount of thermoplastic material required and thereby providing further cost savings.

BRIEF DESCRIPTION OF THE DRAWINGS

FIG. 4 is a perspective view of the assembled device of the present invention as positioned above a conventional baseplate.

FIG. 5 is a sectional view of the assembled device taken along FIGS. 5—5 of FIG. 4.

DETAILED DESCRIPTION OF THE DRAWINGS

Figure 1:
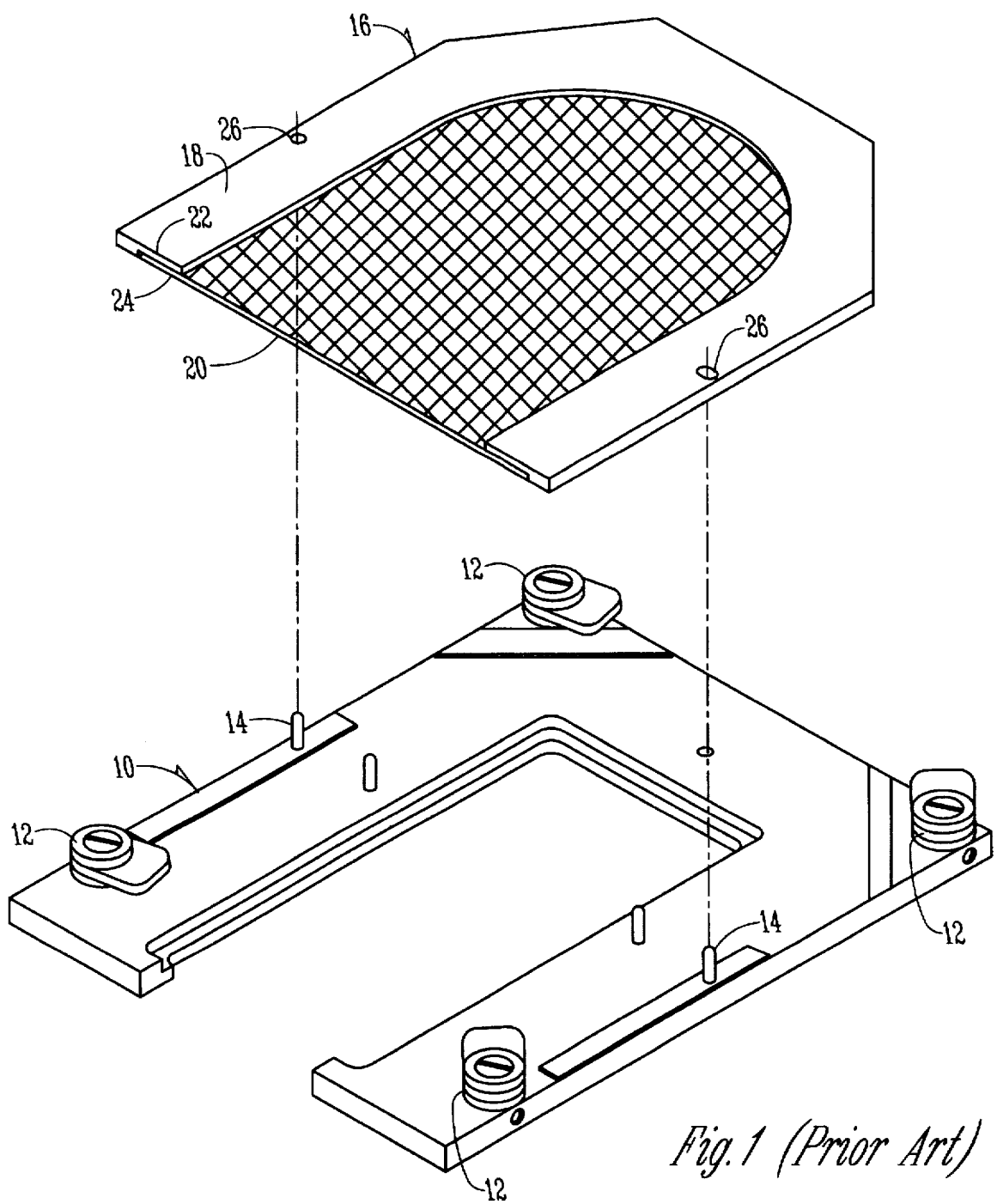
FIG. 1 is an exploded perspective view of a disposable frame and conventional baseplate used in radiation therapy treatment.

Referring to FIG. 1, a conventional baseplate is designated by the reference numeral 10. The baseplate 10 is mounted by conventional means to a table or support surface for radiation therapy, diagnostic imaging, or surgical procedures. The baseplate 10 is generally U-shaped and includes a plurality of pivotal clips 12 for retaining the frame of a head and neck immobilization device, as described further below. The baseplate 10 also includes at least two indexing pins 14 for assuring proper and repeatable positioning of the frame, and thus the patient relative to the treatment table.

A disposable head and neck immobilization device 16 is shown in FIG. 1. The device 16 includes a U-shaped frame 18 to which is adhered a sheet of deformable thermoplastic material 20. The frame 18 has a reduced-thickness inner edge 22 which receives the outer edge 24 of the sheet 20.

Thus, the bottom surface of the frame 18 and the sheet 20 are substantially flush for mounting upon the baseplate 10. As seen in FIG. 1, the overlapped area between the outer edge 24 of the sheet 20 and the inner edge 22 of the frame 18 is relatively substantial, and approximately one inch in width. Since the thermoplastic material is expensive, there is a substantial cost associated with this overlapped area. The frame 18 also includes at least two indexing holes 26 for receiving the indexing pins 14 of the baseplate, thereby assuring proper positioning of the frame 18 upon the baseplate 10.

Figure 2:
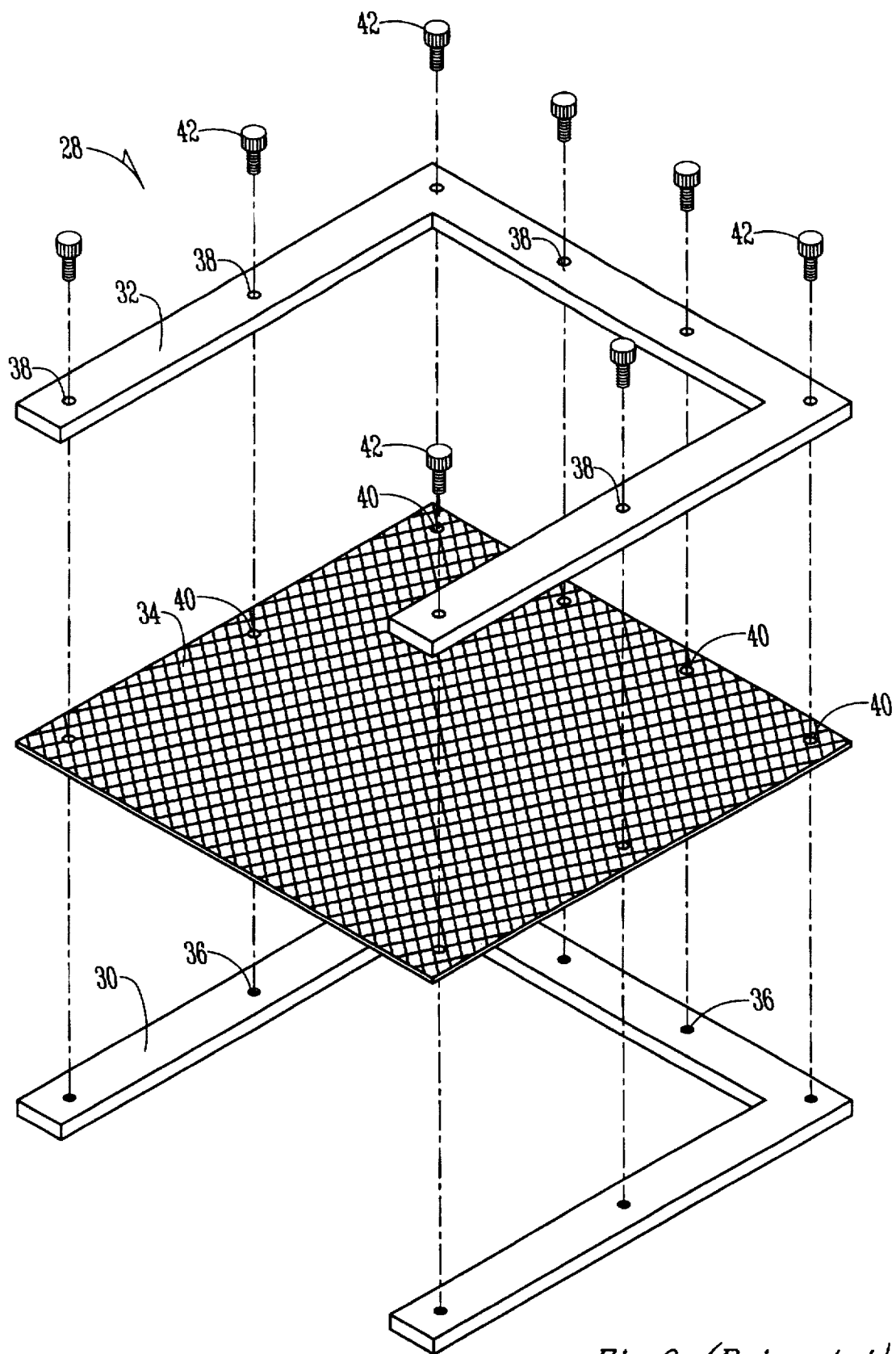
FIG. 2 is an exploded perspective view of a prior art reusable radiation therapy frame.

FIG. 2 shows a conventional reusable head and neck immobilization device 28. The reusable device 28 includes a lower frame 30 and an upper frame 32 between which a sheet 34 of thermoplastic material is sandwiched. The lower frame 30 includes a plurality of threaded holes 36. Corresponding holes 38, 40 are provided in the upper frame 32 and the sheet 34, respectively. A plurality of screws or bolts 42 are adapted to extend through the holes 38, 40 for threaded receipt in the holes 36 for securing the sheet 34 in position between the lower frame 30 and the upper frame 32. The time required to drill the holes 40 in the sheet 34 and to thread each of the screws 42 is considerable, particularly as compared to the disposable frame of FIG. 1.

Figure 3:
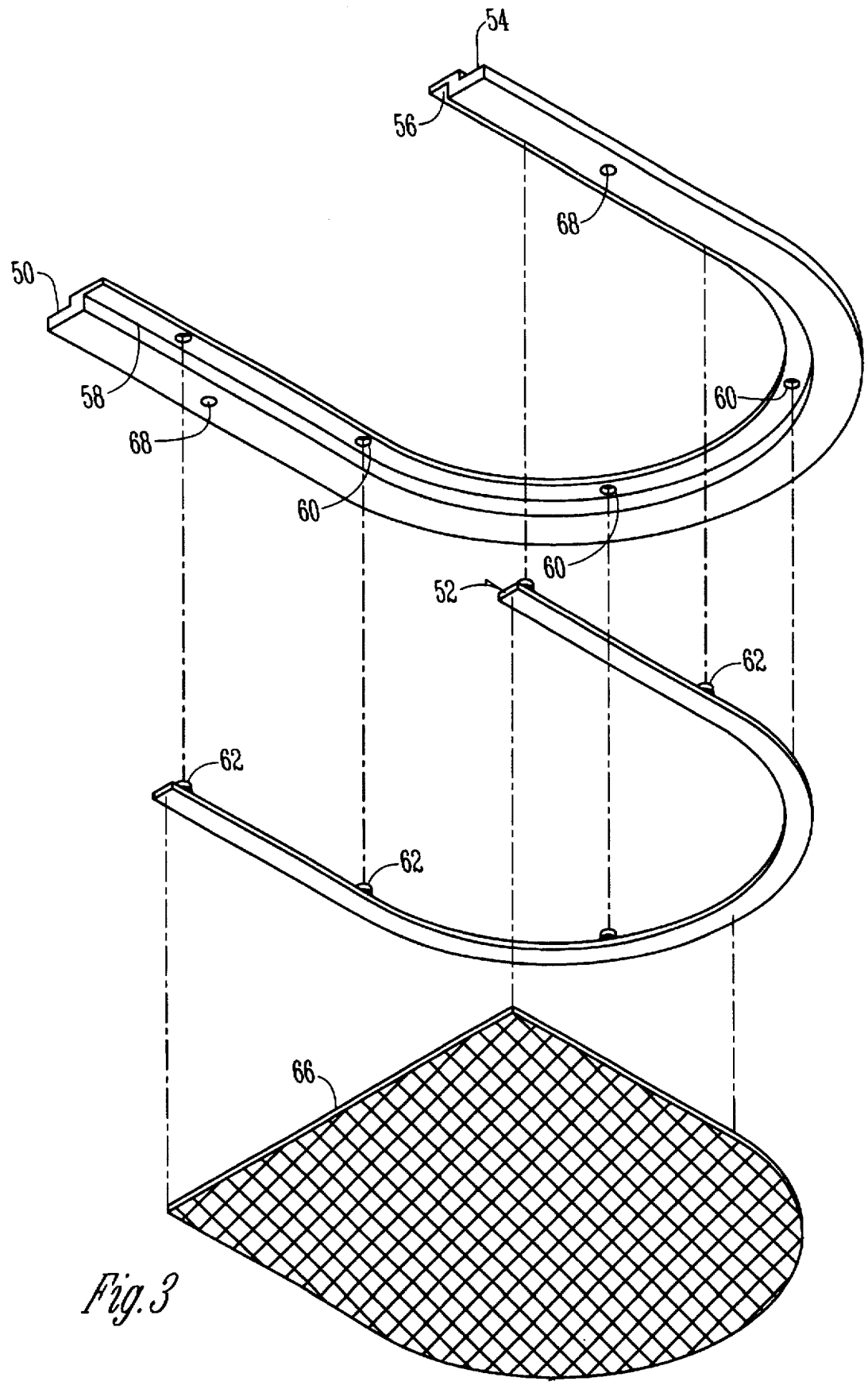
FIG. 3 is an exploded perspective view of the head and neck immobilization device of the present invention.
Figure 6:
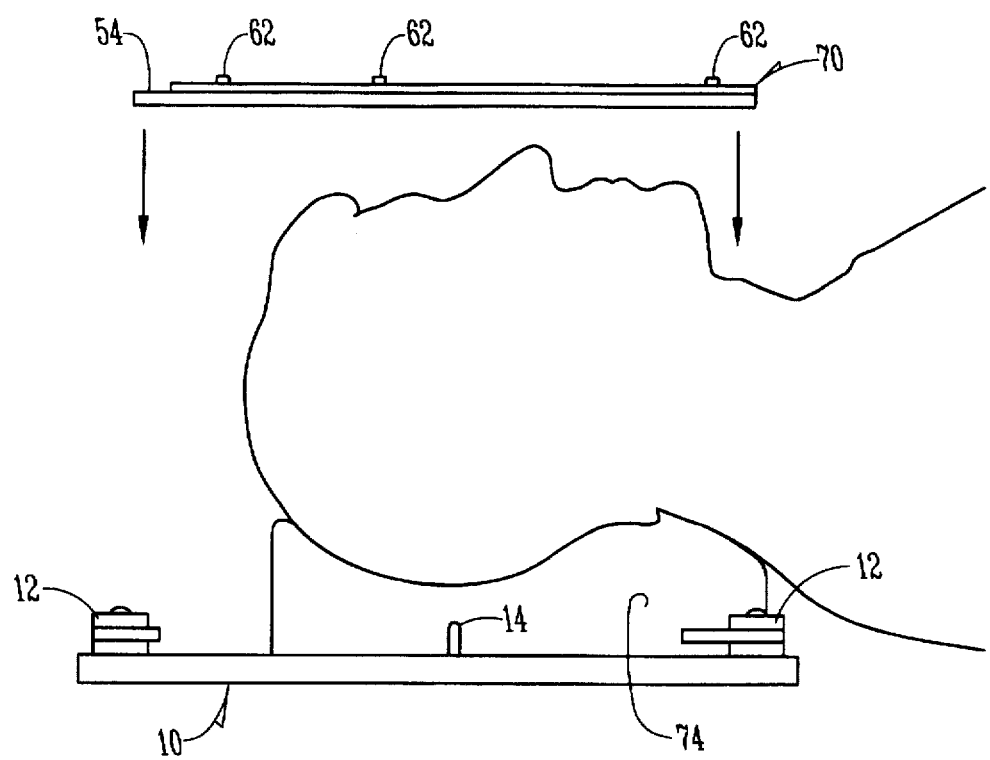
FIG. 6 is a side elevation view of a patient with the assembled device of the present invention prior to deformation of the thermoplastic sheet.

The improved head and heck immobilization system of the present invention includes a U-shaped frame 50 and an insert member 52, as best shown in FIGS. 3–5. The frame includes an outer flange 54 and an offset inner flange 56 which defines a shoulder or recess 58 for matingly receiving the insert 52. A plurality of holes 60 are provided on the inner flange 56 for frictionally receiving a plurality of corresponding pegs 62 on the upper surface of the insert 52. As seen in FIG. 5, each peg 62 includes a rib or ring 64 which allows for a quick and easy snap-fit assembly of the outer and inner flanges 54, 56. Preferably, the pegs 62 and inset 52 have a one-piece molded construction. Alternatively, the pegs 62 can be threadably mounted on the insert 52 with a screw extending upwardly through the insert 52 and into the peg 62, or by the peg 62 having a threaded lower end for receipt in a threaded hole in the insert 52.

A sheet 66 of conventional thermoplastic material is bonded to the bottom surface of the insert 52. Since the insert 52 is preferably made of a plastic material, such as PVC, the sheet 66 can be bonded thereto with a conventional heat press in approximately 15 seconds, which is approximately one minute less than in the prior art frames described above. Alternatively, a hot glue or adhesive bond can be used between the sheet 66 and the insert 52. Another alternative bonding method is high-frequency vibration welding. In any of these bonding methods, the overlapped area between the sheet 66 and the insert 52 is approximately ¼ inch, thereby minimizing the amount of expensive thermoplastic material required.

Figure 7:
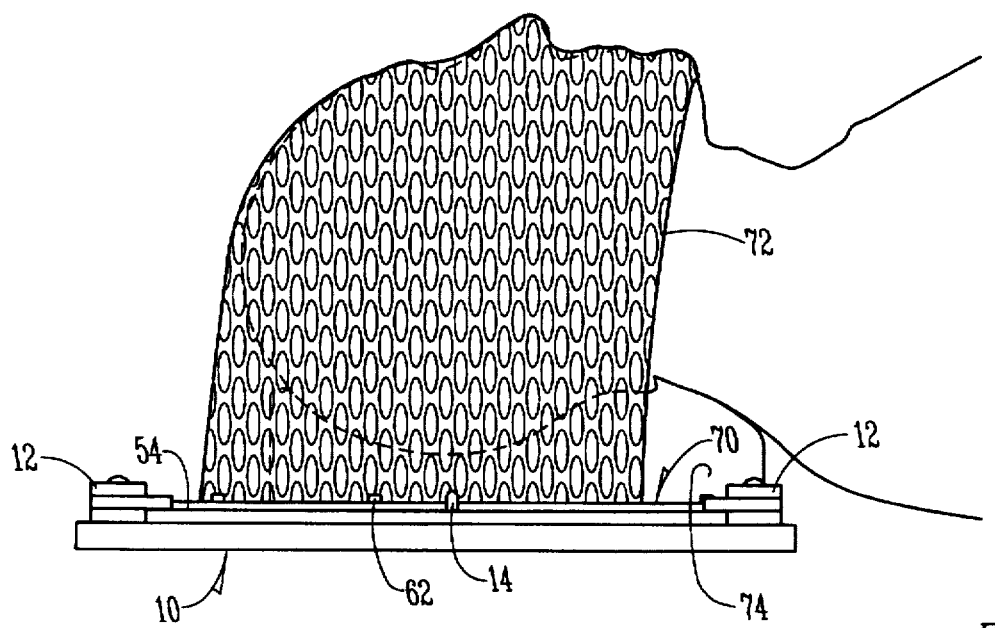
FIG. 7 is a side elevation view showing the device of the present invention in use and mounted on a baseplate after the thermoplastic sheet has been formed into the molded mask for a patient's head.

The frame 50 also includes at least two indexing holes 68 for receipt over the indexing pins 14 on the baseplate 10. The thickness of the outer flange 56 of the frame 50 is such that the frame 50 can be retentively engaged by the clips 12 of the conventional baseplate 10, as seen in FIG. 7.

After the sheet 66 of thermoplastic material is bonded to the insert 52, the insert is mounted in the frame 50 to form an assembly 70. The frame and insert assembly 70 with the attached sheet 66 can then be submerged in warm water, or otherwise heated so as to soften the sheet 66. The assembly 70 is then gently pulled downwardly over the patient's face and mounted on the baseplate 10, thereby forming a molded mask 72 corresponding to the features of a particular patient.

When the sheet 66 of thermoplastic material cools, the mask 72 hardens, thereby preventing movement of the patient's head when the assembly 70 is mounted on the baseplate 10. A cushion 74 may be provided on the baseplate 10 for the patient's comfort.

The insert 52 with the formed mask 72 can be quickly removed from the frame 50 by pushing the pegs 62 out of the holes 60 on the frame 50. Additional masks for different patients can be made using the same frame 50. Thus, while the insert 52 can be discarded after a patient's treatment is complete, the frame 52 is kept and can be reloaded with the individual masks of many different patients.

As compared to the prior art disposable and reusable frames, the present invention uses less of the expensive thermoplastic material since less surface area is required for bonding of the sheet 66 to the insert 52. Also, the disposable insert 52 is less expensive than the disposable frame 18 of the device 16, thereby providing cost savings. Furthermore, the snap-fit assembly of the present invention eliminates the need for a separate frame for each patient, as in the reusable frames 30, 32, and provides for reduced assembly time, thereby providing additional cost savings.

Whereas the invention has been shown and described in connection with the preferred embodiments thereof, it will be understood that many modifications, substitutions, and additions may be made which are within the intended broad of scope of the following claims. For example, the frame 50 can be provided with a slot, in place of the recess 58, into which the insert can slide for retention. Also, the frame and insert assembly with the thermoplastic material can be used to immobilize other parts of the body, in which case the dimensions or shape of the frame and insert may be different.

From the foregoing, it can be seen that the present invention accomplishes at least all of the stated objectives.

What is claimed is:

1. A head and neck immobilization device for use with a treatment table having a baseplate secured thereto, comprising:

a U-shaped frame sized to extend around the sides and top of a patient's head and adapted to be secured to the baseplate;

a U-shaped insert adapted to retentively and detachably mount on the frame; and a mesh sheet attached to the insert and being deformable to form a mask over the patient's head;

the U-shaped insert and the mesh sheet attached thereto constituting a mesh insert assembly which is separable as a unit from the U-shaped frame.

2. The device of claim 1 wherein the frame includes a U-shaped recess for receiving the insert.

3. The device of claim 1 wherein the insert has a plurality of pegs adapted to snap fit into a plurality of holes in the frame.

4. The device of claim 3 wherein the pegs and the insert have a one-piece molded construction.

5. The device of claim 1 wherein the frame has at least two indexing holes adapted to fit over corresponding indexing pins on the baseplate.

6. A method of immobilizing the head of a patient, comprising:

bonding a deformable mesh sheet to a U-shaped insert;

mounting the insert in a U-shaped frame to form an assembly;

positioning the patient's head over a baseplate;

heating the sheet to a softened deformable condition;

pulling the frame and insert assembly downwardly around the patient's head so that the sheet deforms into a mask contouring the patient's head;

attaching the assembled frame and insert to the baseplate; and allowing the sheet to cool and thereby rigidify.

7. The method of claim 6 further comprising removing the insert from the frame, and mounting a second insert to the frame with a second deformable mesh sheeting bonded to the second insert for forming a second mask for a second patient.

8. The method of claim 6 wherein the insert is disposable.

9. The method of claim 6 wherein the mesh sheet is bonded to the insert using heat and pressure.

10. The method of claim 6 wherein the mesh sheet is bonded to the insert by an adhesive.

11. The method of claim 6 wherein the mesh sheet is bonded to the insert by vibration welding.

12. The method of claim 6 wherein the insert and frame are snap fit together.

13. A device for immobilizing a body part of a patient with respect to a support surface, the device comprising:

a rigid assembly mountable on the support surface, and including an outer frame and an insert removably mountable in the frame; and a deformable sheet secured to the insert for forming a mold over the body part of the patient;

the insert and the sheet secured thereto constituting a mesh insert assembly which is separable as a unit from the outer frame.

14. The device of claim 13 wherein the outer frame is usable with a second insert for forming a second patient mold.

15. The device of claim 13 wherein the frame and insert snap fit together.

16. The device of claim 15 wherein one of the insert and frame has pegs and the other of the insert and frame have holes for receiving the pegs such that the insert and the frame snap fit together.

17. The device of claim 13 wherein the frame has a recess for matingly receiving the insert.

18. The device of claim 13 wherein the frame has an outer flange and an inner flange, the outer and inner flanges being offset with respect to one another to define a shoulder for receiving the insert.

19. The device of claim 13 wherein the frame and the insert are each substantially U-shaped.

20. A head and neck immobilization device for use with a treatment table having a baseplate secured thereto, comprising:

a U-shaped frame sized to extend around the sides and top of a patient's head and adapted to be secured to the baseplate;

a U-shaped insert adapted to retentively and detachably mount on the frame;

a mesh sheet attached to the insert and being deformable to form a mask over the patient's head;

the U-shaped insert and the mesh sheet attached thereto constituting a mesh insert assembly which is separable as a unit from the U-shaped frame;

the insert having a plurality of pegs adapted to snap fit into a plurality of holes in the frame; and the pegs each having a friction rib for providing a frictional fit between the insert and the frame.

* * * * *